US009370652B2

(12) United States Patent
Lin et al.

(10) Patent No.: US 9,370,652 B2
(45) Date of Patent: Jun. 21, 2016

(54) DESENSITIZING DEVICE

(71) Applicant: GiMer Medical Co. Ltd., Taipei (TW)

(72) Inventors: Wei-Tso Lin, Taipei (TW); Chen-Tun Wu, Taipei (TW); Chan-Yi Cheng, Taipei (TW); Chi-Heng Chang, Taipei (TW)

(73) Assignee: GiMer MEDICAL CO. LTD., Taipei (TW)

( * ) Notice: Subject to any disclaimer, the term of this patent is extended or adjusted under 35 U.S.C. 154(b) by 119 days.

(21) Appl. No.: 13/949,246

(22) Filed: Jul. 24, 2013

(65) Prior Publication Data

US 2015/0032195 A1 Jan. 29, 2015

(51) Int. Cl.
| | |
|---|---|
| A61N 1/05 | (2006.01) |
| A61N 1/04 | (2006.01) |
| A61F 5/41 | (2006.01) |
| A61H 19/00 | (2006.01) |
| A61N 1/36 | (2006.01) |

(52) U.S. Cl.
CPC ............. *A61N 1/0484* (2013.01); *A61F 5/41* (2013.01); *A61H 19/00* (2013.01); *A61N 1/0456* (2013.01); *A61N 1/0521* (2013.01); *A61N 1/36007* (2013.01); *A61N 1/36014* (2013.01); *A61F 2005/418* (2013.01)

(58) Field of Classification Search
CPC ......... A61N 1/0521; A61F 5/41; A61H 19/00
USPC .......................................................... 607/143
See application file for complete search history.

(56) References Cited

U.S. PATENT DOCUMENTS

| | | | | |
|---|---|---|---|---|
| 5,192,271 A | * | 3/1993 | Kalb et al. | 604/116 |
| 6,015,393 A | * | 1/2000 | Hovland et al. | 600/587 |

* cited by examiner

*Primary Examiner* — Joseph Dietrich
(74) *Attorney, Agent, or Firm* — Muncy, Geissler, Olds & Lowe, P.C.

(57) ABSTRACT

The desensitizing device contains an electrical stimulation member optionally configured on a support member. The electrical stimulation member contains a control circuit, at least two electrodes, and an electricity supply element. The electricity supply element provides electricity to the control circuit, and the control circuit generates a stimulating current to the electrodes. By configuring a male genital with the support member so that the electrodes are in contact with the penis skin, the stimulating current produced by the control circuit is conducted to the electrodes and provides a low-strength subcutaneous nerve stimulation through the penis skin. The subcutaneous nerve is as such temporarily numbed and desensitized.

10 Claims, 6 Drawing Sheets

DESENSITIZING DEVICE

TECHNICAL FIELD OF THE INVENTION

The present invention is generally related to desensitizing devices, and more particular to a device to reduce the sensitivity of male genitals by providing low-strength stimulation.

DESCRIPTION OF THE PRIOR ART

In today's busy society, people's stress significantly affects their private lives. To make the sexual activity more fulfilling, a lot of sex toys are on the market to maintain and enhance people's interest and delight.

One common sex toy is the vibrator. However, a vibrator can only provide stimulation to the tactile sense, and has little effect on the male staying power, which is a major factor to a satisfying intercourse.

To promote male endurance, there are also various medications on the market. However, these medications often contain intoxicant or harmful components, and usually cause undesirable side effects.

SUMMARY OF THE INVENTION

Therefore, a desensitizing device is provided herein, which contains an electrical stimulation member optionally configured on a support member. The electrical stimulation member contains a control circuit, at least two electrodes, and an electricity supply element. The electricity supply element provides electricity to the control circuit, and the control circuit generates a stimulating current to the electrodes. By configuring a male genital with the support member so that the electrodes are in contact with the penis skin, the stimulating current produced by the control circuit is conducted to the electrodes and provides a low-strength subcutaneous nerve stimulation through the penis skin. The subcutaneous nerve is as such temporarily numbed and desensitized, thereby enhancing the staying power of male genitals during intercourse. Since no medication is employed, potential undesirable side effects are avoided.

In addition to providing low-strength subcutaneous nerve stimulation to male genitals, the present invention can also be applied to other body parts (e.g., a wrist, an elbow, etc.) for low-strength subcutaneous nerve stimulation. In these applications, the electrodes are attached directly to the desired body part. The stimulating current produced by the control circuit is conducted to the electrodes and provides a low-strength subcutaneous nerve stimulation through the skin of the desired body part. The subcutaneous nerve is as such temporarily numbed and desensitized so as to ease the neuralgia.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become apparent to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

Figure 1:
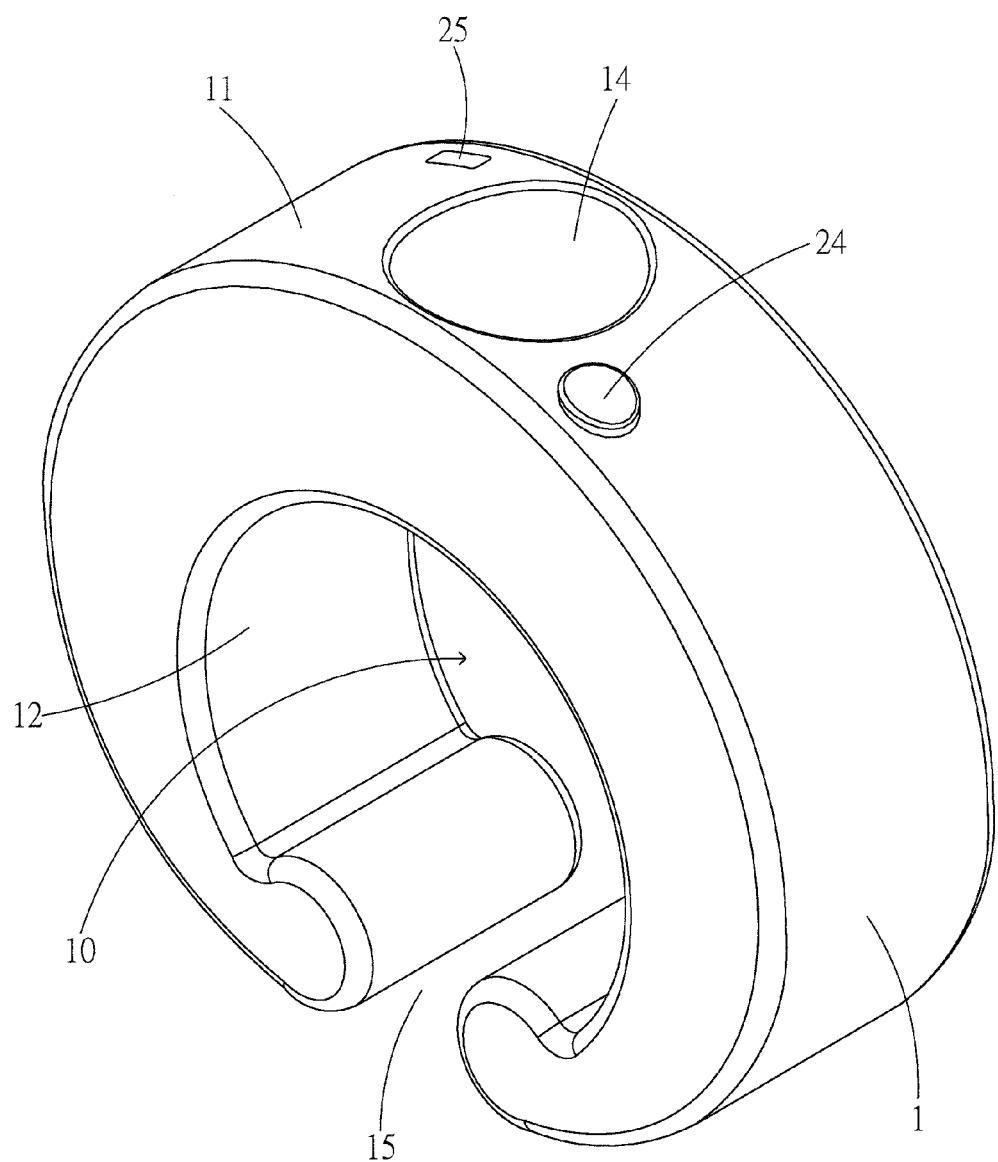
FIG. 1 is a perspective diagram showing a desensitizing device according to a first embodiment of the present invention.
Figure 2:
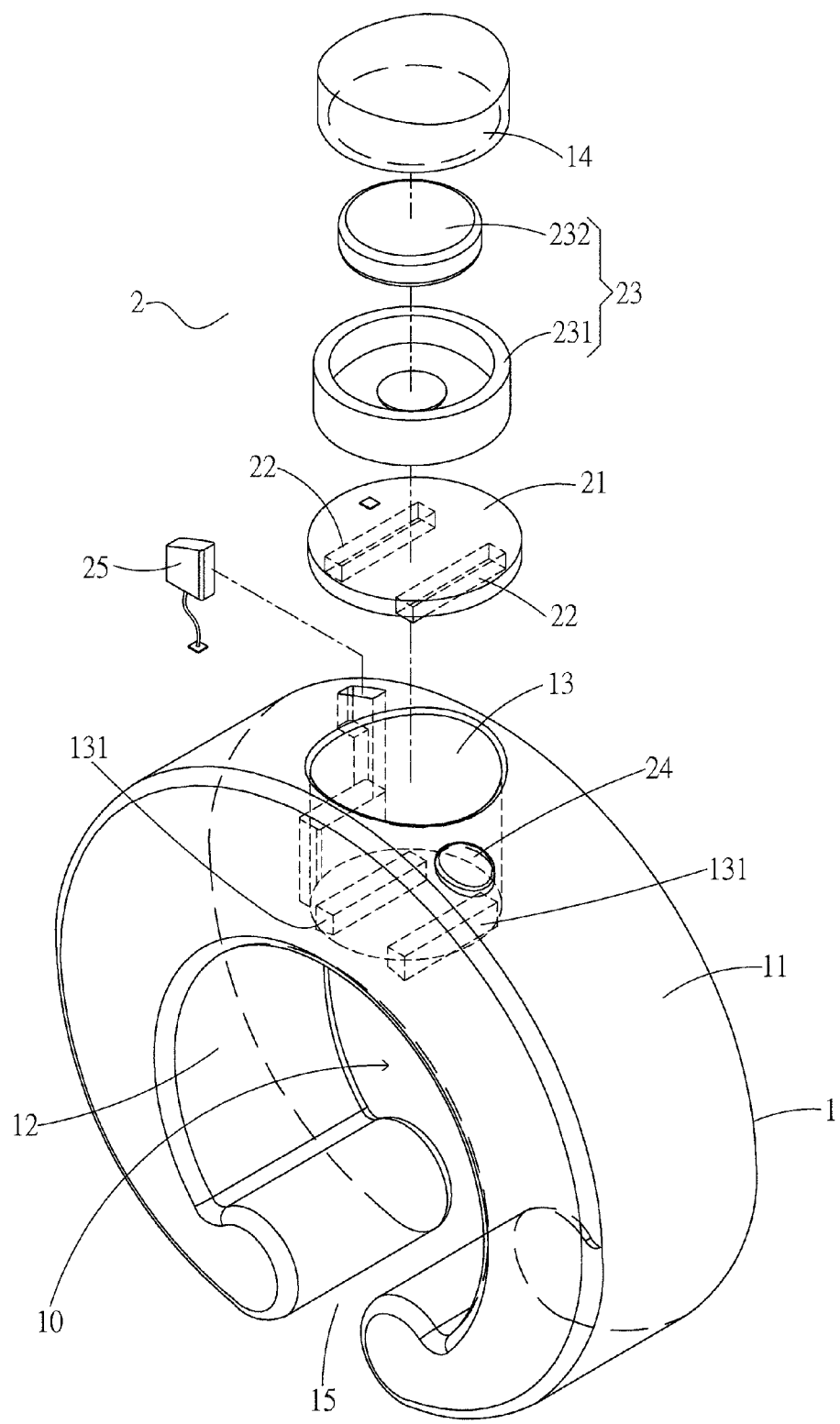
FIG. 2 is a perspective break-down diagram showing the various components of the desensitizing device of FIG. 1.
Figure 3:
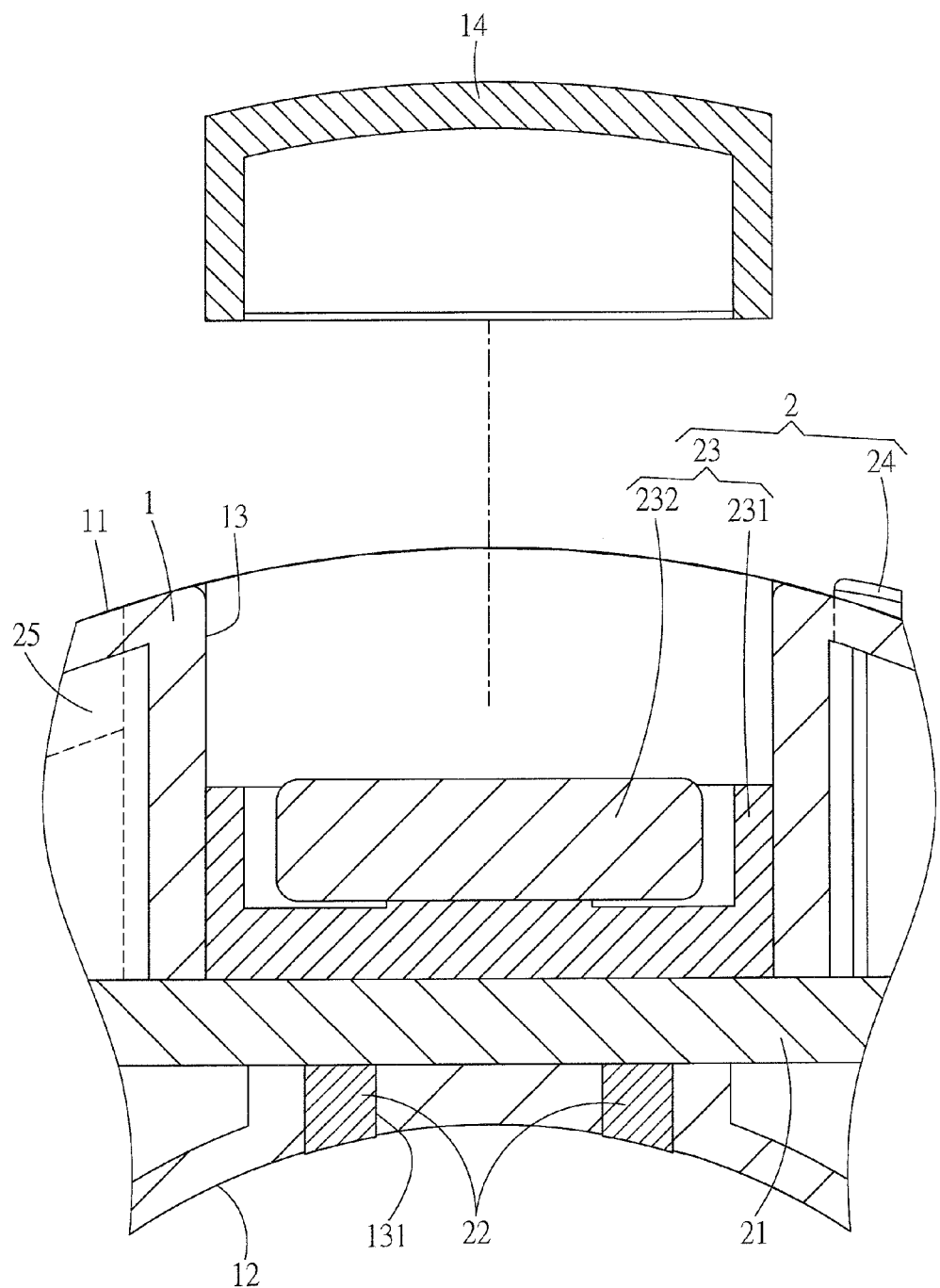
FIG. 3 is a partial sectional diagram showing the desensitizing device of FIG. 1.
Figure 4:
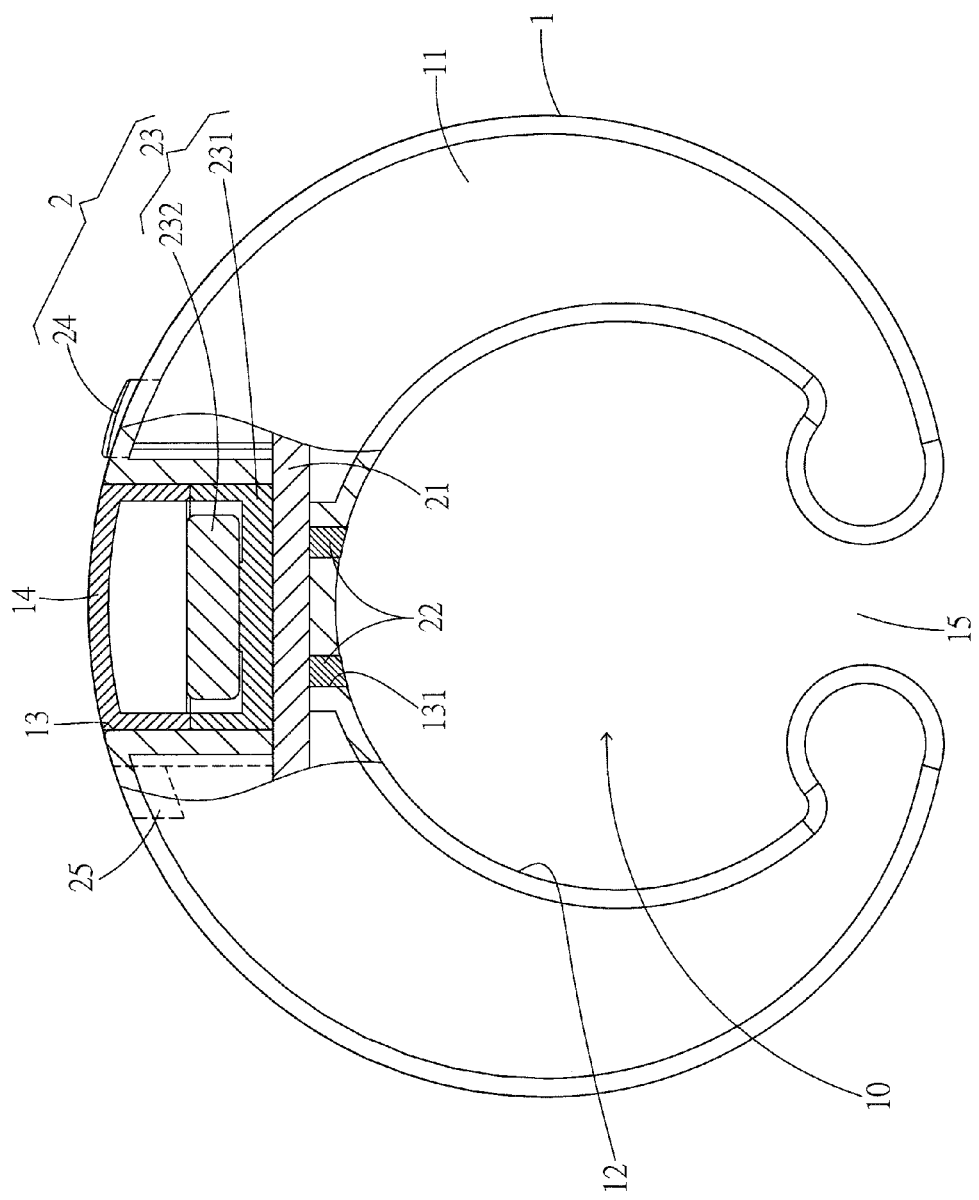
FIG. 4 is a partial sectional diagram showing the desensitizing device of FIG. 1.

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

As shown in FIGS. 1 to 4, a desensitizing device according to a first embodiment of the present invention contains an electrical stimulation member 2 optionally configured on a support member 1. The support member 1 can be ring-shaped or in other appropriate shape.

The support member 1 has an outer circumference 11, an inner circumference 12, and a through channel 10 surrounded by the inner circumference 12. The support member 1 has an accommodation space 13 with a circular first opening on the outer circumference 11 sealed by a cover 14, and at least two linear second openings 131 on the inner circumference 12 so that the accommodation space 13 is connected to the through channel 10. The support member 1 is made of a flexible material and can be configured into a C-like shape with an axially-oriented linear opening 15 so that the linear opening 15 can be elastically broadened.

The electrical stimulation member 2 is housed in the accommodation space 13, and contains a control circuit 21, at least two electrodes 22, and an electricity supply element 23. The electricity supply element 23 can contain a removable battery or a built-in rechargeable battery, and is electrically connected to the control circuit 21 so as to provide electricity to the control circuit 21. In the present embodiment, the electricity supply element 23 contains a removable battery 232 and a battery chamber 231. The battery chamber 231 has a positive terminal and a negative terminal, both connected to the control circuit 21. The battery 232 is accommodated in the battery chamber 231 and the battery 232's positive and negative terminals are connected to the battery chamber 231's positive and negative terminals, respectively. The at least two electrodes 22 are electrically connected to the control circuit 21, and are exposed to the through channel 10 on the inner circumference 12 through the second openings 131, respectively. With the electricity provided by the electricity supply element 23, the control circuit 21 generates and delivers a stimulating current to the electrodes 22.

The stimulating current produced by the control circuit 21 can be a high-frequency signal between 200 KHz and 800 KHz, or a low-frequency signal between 0.5 Hz and 1 KHz (preferably between 2 Hz and 30 Hz), or a mixed signal with a high-frequency component and a low-frequency component. The high-frequency component is between 200 KHz and 800 KHz, and the low-frequency component is between 0.5 Hz and 1 KHz (preferably between 2 Hz and 30 Hz). The high-frequency or low frequency signal of the stimulating current can be a continuous wave or a train of intermittent pulses. The wave can be a sinusoidal wave, a triangular wave, a square wave, or one with an appropriately shaped waveform.

As the electrical stimulation member 2 is accommodated in the accommodation space 13, the control circuit 21 can be placed on a bottom side of the accommodation space 13. The electrodes 22 are electrically connected to a bottom side of the control circuit 21, configured in the second openings 131, respectively, and exposed from the inner circumference 12. The electricity supply element 23 has the battery chamber 231 electrically connected to a top side of the control circuit 21, and the battery 232 is placed in the battery chamber 231. The first opening of the accommodation space 13 is then sealed by the cover 14 so that the electrical stimulation member 2 is tightly housed in the accommodation space 13.

The electrical stimulation member 2 further contains a switch 24 and an indicator lamp 25. The switch 24 is electrically connected to the control circuit 21 for turning the control circuit 21 on and off, and is exposed from the outer circumference 11 on the support member 1. The indicator lamp 25 is also electrically connected to the control circuit 21 and is exposed from the outer circumference 11 on the support member 1.

By threading a male genitals through the through channel 10 of the support member 1 so that the electrodes 22 are in contact with the penis skin, the stimulating current produced by the control circuit 21 when the electrical stimulation member 2 is turned on is conducted to the electrodes 22 and provides a low-strength subcutaneous nerve stimulation through the penis skin. The subcutaneous nerve is as such temporarily numbed and desensitized, thereby enhancing the staying power of male genitals during intercourse. Since no medication is employed, potential undesirable side effects are avoided.

Figure 5:
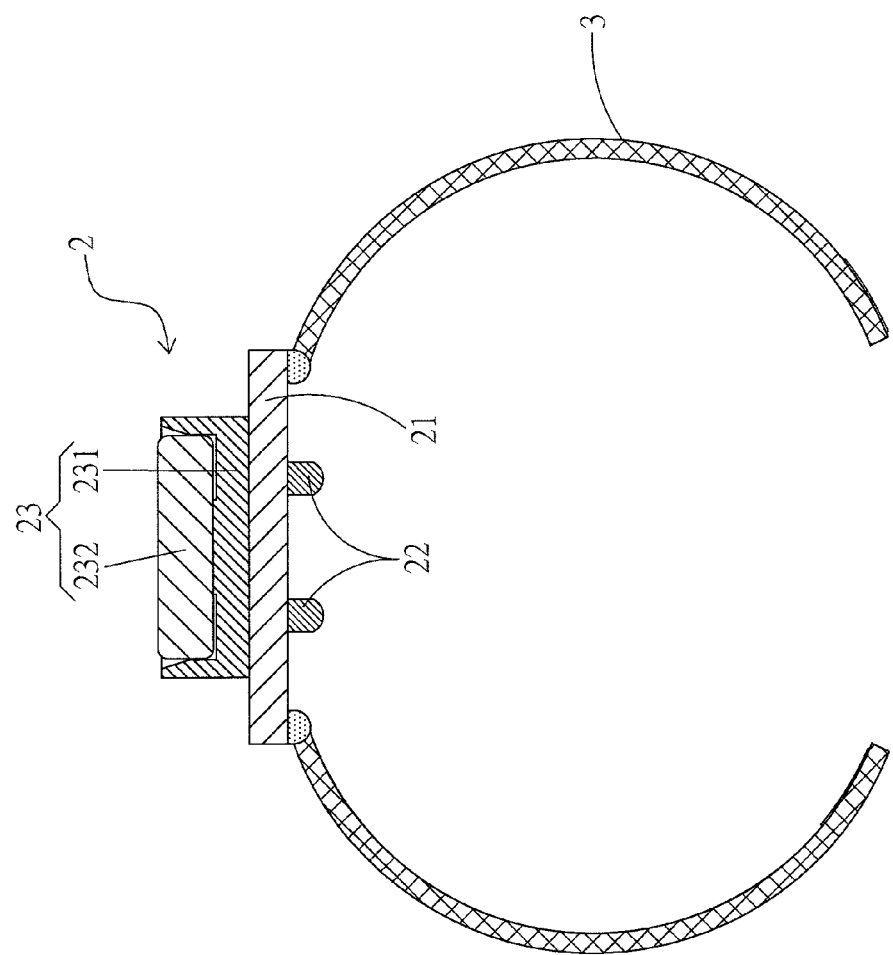
FIG. 5 is a sectional diagram showing a desensitizing device according to a second embodiment of the present invention.

FIG. 5 depicts a second embodiment of the present invention. As illustrated, a desensitizing device of the present embodiment has an electrical stimulation member 2 configured on a belt-like support member 3. The support member 3 girdles a male genital so that the electrodes 22 of the electrical stimulation member 2 are in contact with the penis skin. The stimulating current produced by the control circuit 21 is conducted to the electrodes 22 and provides a low-strength subcutaneous nerve stimulation through the penis skin. The subcutaneous nerve is as such temporarily numbed and desensitized.

Figure 6:
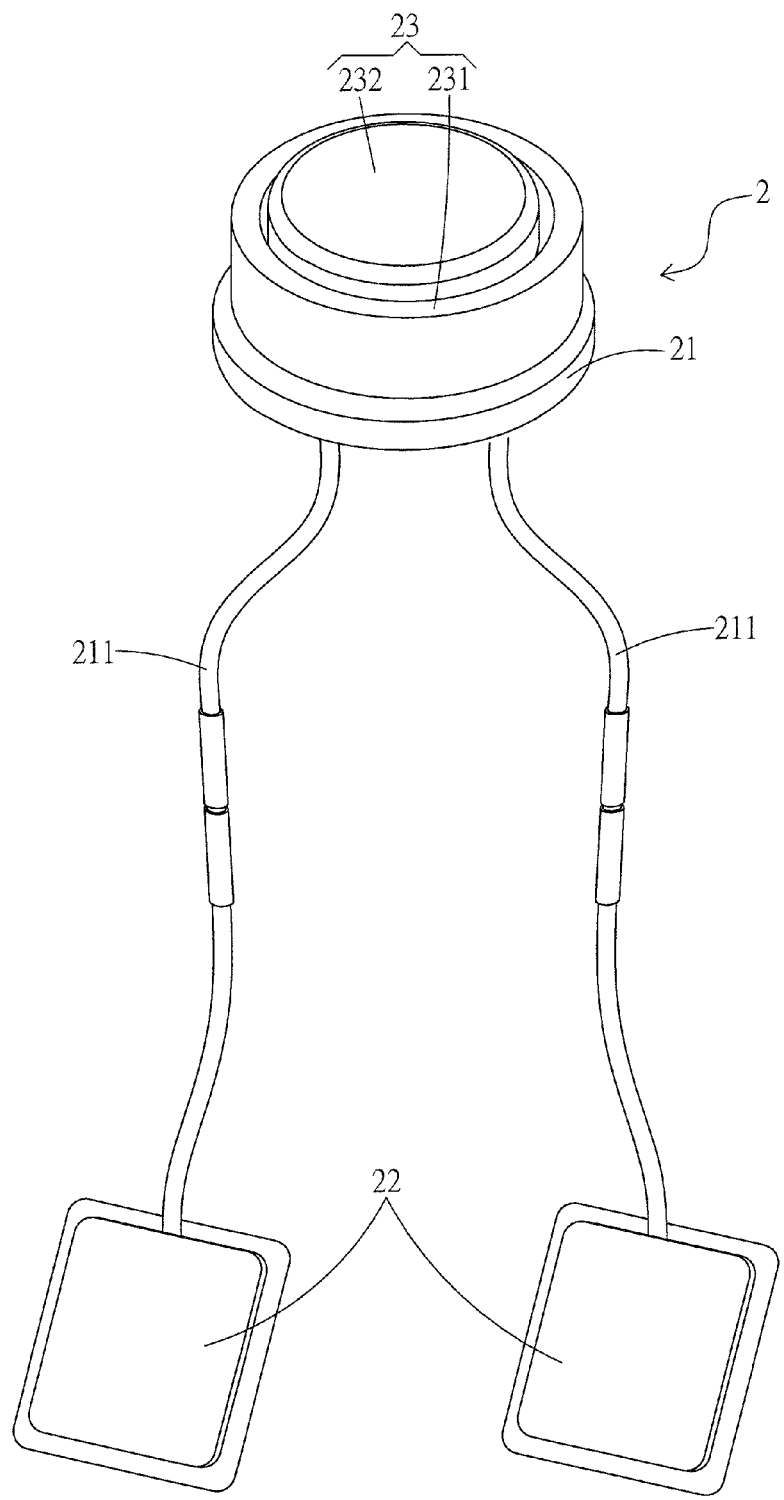
FIG. 6 is a perspective diagram showing a desensitizing device according to a third embodiment of the present invention.

FIG. 6 depicts a third embodiment of the present invention. As illustrated, a desensitizing device of the present embodiment has an electrical stimulation member 2 that is applied independently without a support member. The two electrodes 22 of the control circuit 21 are configured in two pads and extended by two transmission wires 211 so that the electrodes 22 can be attached to the penis skin directly. The stimulating current produced by the control circuit 21 is conducted to the electrodes 22 and provides a low-strength subcutaneous nerve stimulation through the penis skin. The subcutaneous nerve is as such temporarily numbed and desensitized.

In addition to providing low-strength subcutaneous nerve stimulation to male genitals, the high-frequency current produced by the control circuit 21 can also be applied to other body parts (e.g., a wrist, an elbow, etc.) for low-strength subcutaneous nerve stimulation. In these applications, the electrodes 22 are attached directly to the desired body part. The stimulating current produced by the control circuit 21 is conducted to the electrodes 22 and provides a low-strength subcutaneous nerve stimulation through the skin of the desired body part. The subcutaneous nerve is as such temporarily numbed and desensitized so as to ease the neuralgia.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

We claim:

1. A desensitizing device, comprising an electrical stimulation member; wherein the electrical stimulation member comprises:
   a control circuit producing a stimulating current comprising a first frequency signal between 200 KHz and 800 KHz;
   at least two electrodes configured to be attached to a user's penis skin and electrically connected to the control circuit receiving the simulating current from the control circuit and applying the stimulating current to the penis skin, wherein the stimulating current is provided to a subcutaneous nerve through the penis skin, and the subcutaneous nerve is temporarily desensitized; and
   an electricity supply unit electrically connected to the control circuit for providing electricity to the control circuit.

2. The desensitizing device according to claim 1, wherein the first frequency signal of the stimulating current is a continuous wave.

3. The desensitizing device according to claim 1, wherein the first frequency signal of the stimulating current is a train of intermittent pulses.

4. The desensitizing device according to claim 1, further comprising a support member; wherein
   the support member has an outer circumference, an inner circumference, a through channel surrounded by the inner circumference, and an accommodation space with a first opening on the outer circumference and at least two second openings on the inner circumference; the support member is made of a flexible material and is configured into a substantially ring-like shape; and the electrodes are exposed from the inner circumference through the second openings, respectively.

5. The desensitizing device according to claim 4, wherein the support member is belt-shaped.

6. The desensitizing device according to claim 1, wherein the electrodes are extended from the control circuit by a plurality of transmission wires, respectively.

7. The desensitizing device according to claim 1, wherein the electricity supply unit comprises a removable battery.

8. The desensitizing device according to claim 1, wherein the electricity supply unit comprises a built-in rechargeable battery.

9. The desensitizing device according to claim 1, wherein the stimulating current further comprises a second frequency signal between 0.5 Hz and 1 KHz.

10. The desensitizing device according to claim 1, wherein the stimulating current further comprises a second frequency signal between 2 Hz and 30 Hz.

* * * * *